(12) United States Patent
Davis, Jr.

(10) Patent No.: US 9,144,898 B1
(45) Date of Patent: Sep. 29, 2015

(54) FAUCET SEAT AND SPRING INSERTER

(71) Applicant: Winford Davis, Jr., Vanndale, AR (US)

(72) Inventor: Winford Davis, Jr., Vanndale, AR (US)

( * ) Notice: Subject to any disclaimer, the term of this patent is extended or adjusted under 35 U.S.C. 154(b) by 341 days.

(21) Appl. No.: 13/718,164

(22) Filed: Dec. 18, 2012

(51) Int. Cl.
*B25B 27/26* (2006.01)
*B25B 27/02* (2006.01)
*B25B 27/28* (2006.01)
*B25B 27/24* (2006.01)
*A61B 17/29* (2006.01)
*B25B 27/06* (2006.01)

(52) U.S. Cl.
CPC ............... *B25B 27/26* (2013.01); *B25B 27/023* (2013.01); *A61B 17/29* (2013.01); *B25B 27/06* (2013.01); *B25B 27/24* (2013.01); *B25B 27/28* (2013.01)

(58) Field of Classification Search
CPC .... B25B 27/023; B25B 27/10; B25B 27/062; E03C 1/0412
USPC ........... 29/225, 230, 222, 238, 214–215, 256, 29/213.1; 81/3.07, 3.15, 3.33, 3.45, 3.57, 81/3.05

See application file for complete search history.

(56) References Cited

U.S. PATENT DOCUMENTS

| | | | | |
|---|---|---|---|---|
| 3,584,365 | A | * | 6/1971 | Cuen et al. ...................... 29/256 |
| 3,844,291 | A | * | 10/1974 | Moen .............................. 606/206 |
| 5,915,740 | A | * | 6/1999 | Weitner ........................ 29/213.1 |

* cited by examiner

*Primary Examiner* — Lee D Wilson
*Assistant Examiner* — Seahee Yoon
(74) *Attorney, Agent, or Firm* — Taylor English Duma LLP

(57) ABSTRACT

A plumbing device includes a housing that fits over a rod according to examples of the present disclosure. The rod is movably positioned in the housing. A pin connected to the rod is contained within an elongate opening in the outer surface of the housing. The pin serves as a stop for the rod in an extended position and retracted position.

9 Claims, 3 Drawing Sheets

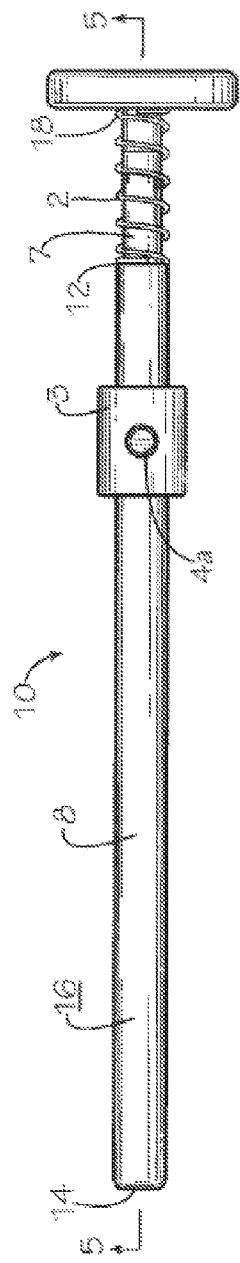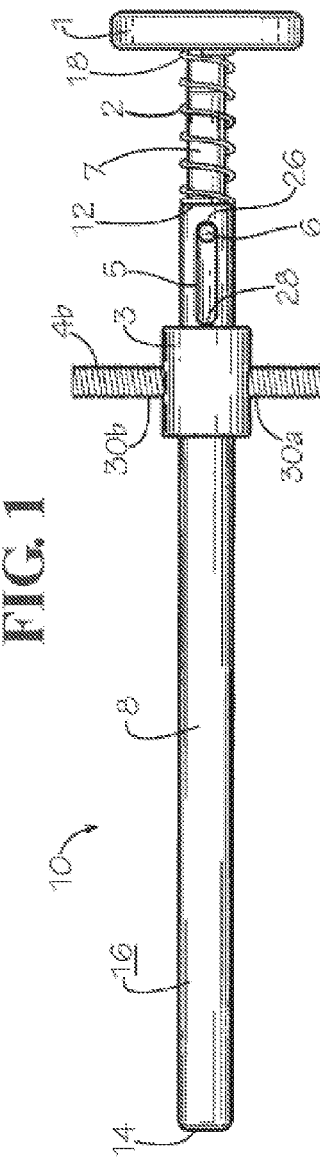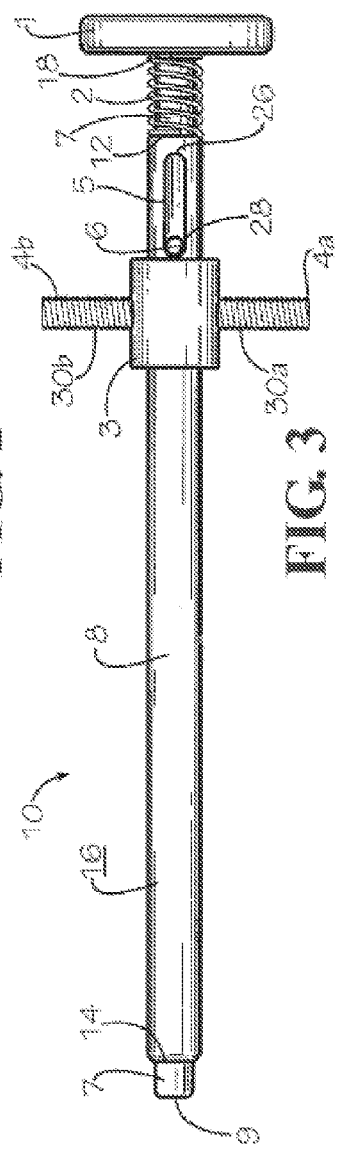

FAUCET SEAT AND SPRING INSERTER

FIELD OF THE INVENTION

This disclosure relates to a plumbing tool for faucets. More specifically, this disclosure relates to a plumbing tool for inserting a faucet seat and spring into a faucet housing.

BACKGROUND

Faucets are devices which control a flow of liquid from a pipe or container by opening or closing an orifice in the faucet housing. Some faucets utilize spring-loaded seals, which have a faucet seat and a seal spring, to keep water from running when the faucet is off. When the seals wear out, the faucet leaks and the seals must be replaced.

SUMMARY

Disclosed is a plumbing device which overcomes difficulties associated with inserting a faucet seat and seal spring into a faucet housing. The plumbing device includes a housing enclosing a rod, the rod movable upwards and downwards within the housing.

A first end of the rod is connected to a knob in various examples. In examples, the plumbing tool includes a sleeve having adjustable handle bars positioned on the outer surface of the housing. When the knob and handle bars of the sleeve are squeezed together, the squeezing causes the knob to push the second end of the rod downward from within the housing and through the housing such that the second end of the rod extends beyond an end of the housing to engage a faucet seat and seal spring. A tool spring enclosing the rod and positioned between the knob and the housing biases the rod to retract back into position with the second end of the rod within the housing.

Various implementations described in the present disclosure may include additional systems, methods, features, and advantages, which may not necessarily be expressly disclosed herein but will be apparent to one of ordinary skill in the art upon examination of the following detailed description and accompanying drawings. It is intended that all such systems, methods, features, and advantages be included within the present disclosure and protected by the accompanying claims.

BRIEF DESCRIPTION OF THE DRAWINGS

The features and components of the following figures are illustrated to emphasize the general principles of the present disclosure. Corresponding features and components throughout the figures may be designated by matching reference characters for the sake of consistency and clarity.

FIG. 1 is a side view of the plumbing device including a rod, a housing, a spring, and a sleeve with adjustable handles according to examples of the present disclosure.

FIG. 2 is a front view of the example plumbing device of FIG. 1 in a retracted position according to examples of the present disclosure.

FIG. 3 is a front view of the example plumbing device of FIG. 1 in an extended position according to examples of the present disclosure.

DETAILED DESCRIPTION

Figure 4:
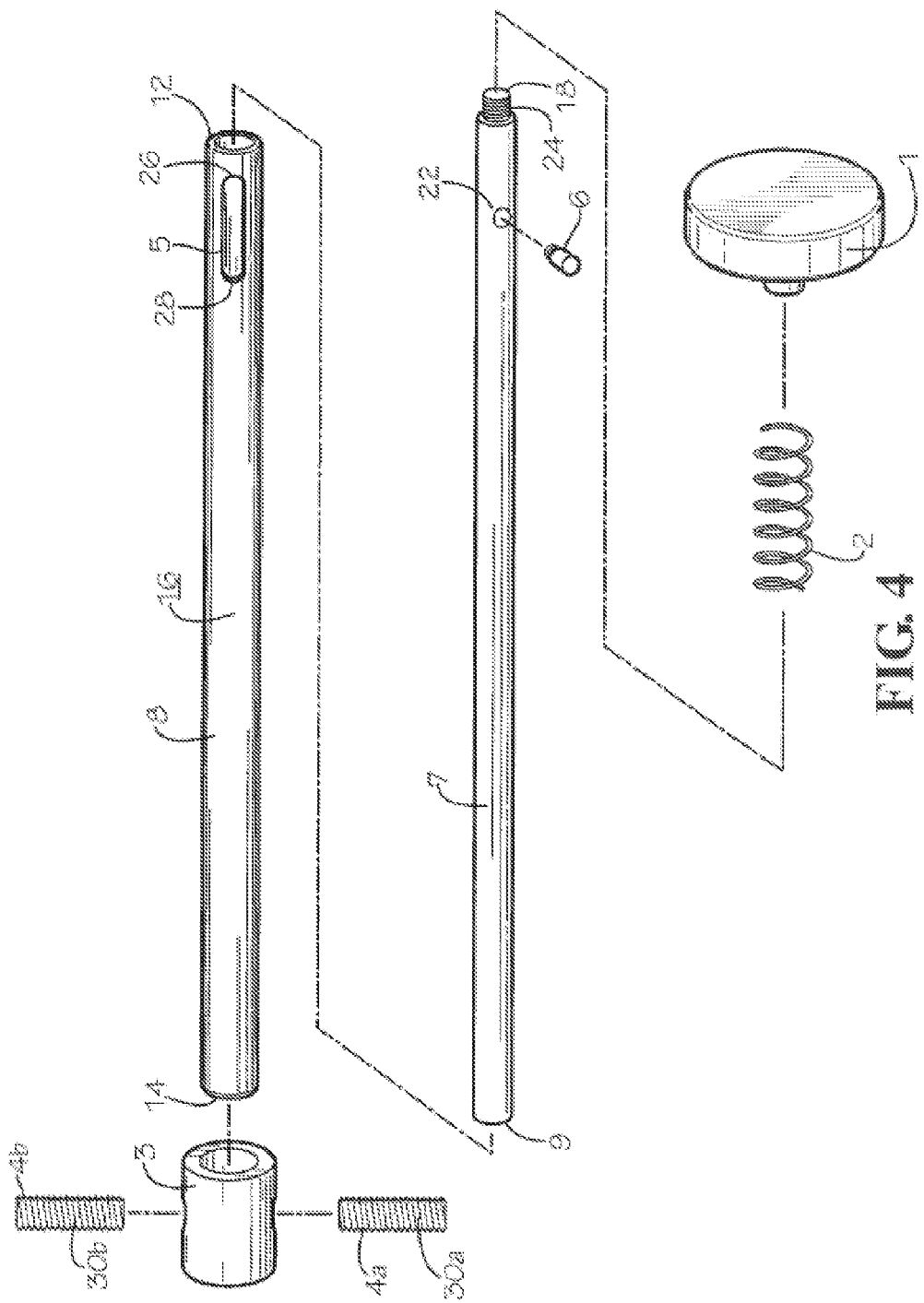
FIG. 4 is an exploded assembly view of the example plumbing device of FIG. 1 according to examples of the present disclosure.

The plumbing device of the current disclosure makes it easier to remove and insert a faucet seat and seal spring from a faucet housing because a user does not have to use his or her fingers to replace the faucet seat and seal spring.

One example of a plumbing device 10 is disclosed and described in FIG. 1. As shown in the example of FIG. 1, the plumbing device 10 includes a knob 1, a tool spring 2, a sleeve 3 with handle 4a and handle 4b, a rod 7, and a housing 8. Directional references such as "up," "down," "top," "left," "right," "front," "back," "above," "below," and "corners," among others are intended to refer to the orientation as shown and described in the figure (or figures) to which the components and directions are referencing.

In various examples, the rod 7 includes a first end 18 (shown in FIG. 4) and a second end 9 (shown in FIG. 3). In various examples, the rod 7 includes threading 24 at the first end 12 (shown in FIG. 4). In various examples, the knob 1 engages threading 24 to connect the knob 1 to the first end 18 of the rod 7. In various examples, the rod 7 is a solid rod. In various examples, the tool spring 2 is positioned on the rod 7 in between a first end 12 of the housing 8 and the knob 1. The housing 8 includes a first end 13, a second end 14, and an outer surface 16 extending from the first end 13 to the second end 14. In various examples, the housing 8 is an elongated tube with a hollow center extending from the first end 12 to the second end 14. As shown in FIG. 1, in various examples, a portion of the rod 7 is positioned in the housing 8 and the rod 7 is movably positioned within the housing 8.

As shown in FIG. 1, in various examples, the tool spring 2 is positioned on the rod 7 between the housing 8 and the knob 1 such that the tool spring 2 surrounds a portion of the rod 7. In various examples, movement of the knob 1 towards the housing 8 influences the rod 7 to move downward through the housing 8.

As shown in FIG. 1, in various examples, the plumbing device 10 includes the adjustable sleeve 3 with two handle bars 4a,b. In various examples, the handle bars 4a,b are approximately parallel to each other on each side of the sleeve 3. In various examples, each of the handles 4a,b includes threading 30a,b that engages the adjustable sleeve 3 such that the handles 4a,b screw inward against the adjustable sleeve 3. In various examples, the handles 4a,b are engageable with the outer surface 16 of the housing 8 such that the handles 4a,b hold the adjustable sleeve 3 in place at a desired location along the outer surface 16 after adjustably positioning the adjustable sleeve 3 on the outer surface 16 of the housing 8 between the first end 12 and the second end 14.

As previously described, the two screw-in handle bars 4a,b are engageable and tighten up on the housing 8 to hold the adjustable sleeve 3 in place on the housing 8. In various examples, squeezing the knob 1 towards the handles 4a,b compresses the spring and influences the rod 7 to move downward through the second end 14 of the housing 8.

As shown in FIG. 1, in various examples, the housing 8 defines an elongated opening 5 within the outer surface 16 of the housing 8. In various examples, the elongated opening has a first end 26 and a second end 28. In various examples, the rod 7 defines a pin opening 22 (shown in FIG. 4) extending transversely through the rod 7. In various examples, a pin 6 is connected to the rod 7. In various examples, the pin is fit into the pin opening 22.

As previously described, the pin 6 is fitted into the pin opening 22 extending transversely through the rod 7. In various examples, the pin 6 extends transversely from the rod 7 when the pin 6 is connected to the rod 7. In various examples, the pin 6 connected to the rod 7 extends through the elongated opening 5 of the housing 8 and is contained in the elongated opening 5 of the housing 8. The pin 5 is movably positioned as the rod 7 is movably positioned in the housing 8 such that when the rod 7 is movably positioned through the housing 8, the pin 5 moves within the elongated opening 5 between the first end 26 and the second end 28.

In various examples, the rod 7 is movably positioned within the housing 8 between a retracted position, shown in FIG. 2, and an extended position, shown in FIG. 3. In the extended position, the first end 18 of the rod 7 is disposed above the first end 12 of the housing 8 and the second end 9 of the rod 7 is disposed below the second end 14 of the housing 8, as shown in FIG. 3. In various examples, the second end 9 of the rod 7 is disposed approximately 5/16 of an inch below the second end 14 of the housing 8. As shown in FIG. 3, in various embodiments, in the extended position, the pin 5 engages the second end 28 of the elongated opening 5.

Figure 5:
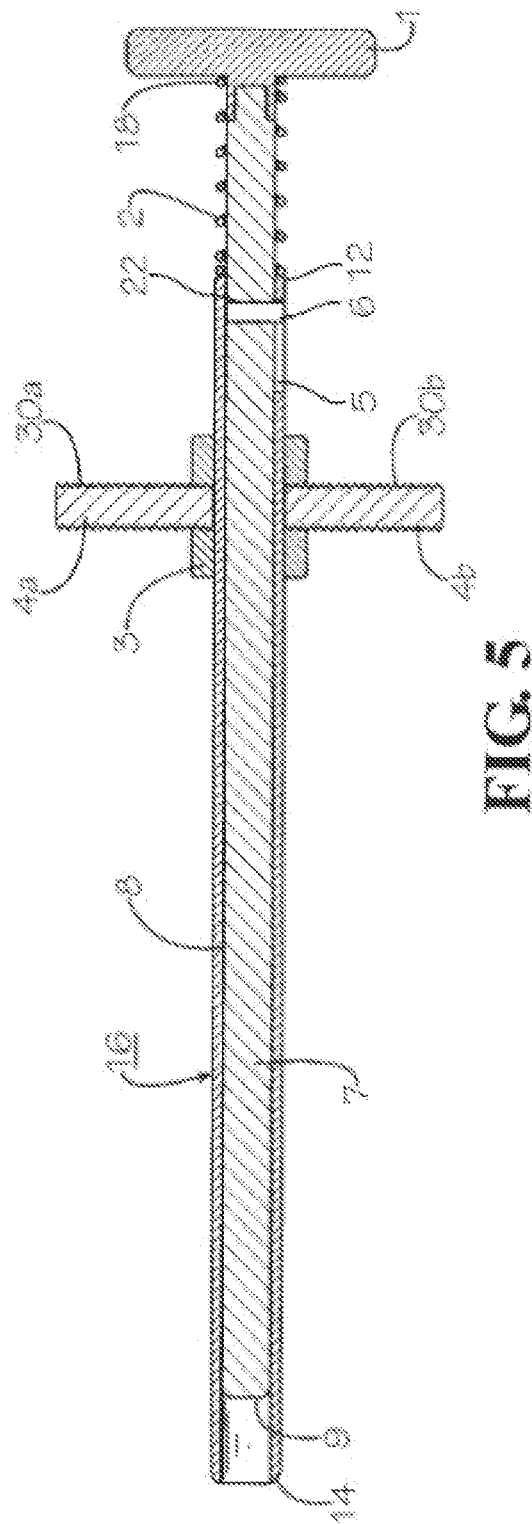
FIG. 5 is a cross-sectional view of the example plumbing device of FIG. 1 taken along line 5-5 in FIG. 2 according to examples of the present disclosure.

In various examples, the second end 9 disposed below the second end 14 enables the second end 9 to engage a seat and spring to be inserted into the faucet's housing. In the retracted position, the first end 18 of the rod 7 is disposed above the first end 12 of the housing 8 and the second end 9 is disposed within the housing 8 above the second end 14 of the housing 8, as is partially shown in FIG. 1 and fully shown FIG. 5. As shown in FIG. 2, in various examples, in the retracted position, the pin 5 engages the first end 26 of the elongated opening 5. In various examples, the tool spring 2 biases the rod 7 to the retracted position through the knob 1 such that the rod 7 retracts the second end 9 of the rod 7 within the housing 8 when the knob 1 is released by a user.

What is claimed is:

1. A plumbing device comprising:
   a rod;
   a knob, the rod connected to the knob at a first end of the rod;
   a housing, the rod enclosed in the housing, the housing defining an elongated opening;
   a spring surrounding the rod, the spring positioned between the knob and the housing;
   a pin connected to the rod proximate to the first end of the rod, the pin extending transverse to the rod and extending through the elongated opening of the housing, the pin having a length less than a diameter of the housing; and
   a sleeve adjustably positioned on an outer surface of the housing, the sleeve having handles engageable with the outer surface of the housing.

2. The plumbing device of claim 1, wherein the rod is movable to a retracted position, and wherein in the retracted position, the pin is engaged with a first end of the elongated opening.

3. The plumbing device of claim 2, wherein the rod is movable to an extended position, and wherein in the extended position, the pin is engaged with a second end of the elongated opening.

4. The plumbing device of claim 1, wherein in an extended position, the first end of the rod is disposed above a first end of the housing and a second end of the rod is disposed below a second end of the housing.

5. The plumbing device of claim 1, wherein in a retracted position, the first end of the rod is disposed above a first end of the housing and a second end of the rod is disposed within the housing above a second end of the housing.

6. The plumbing device of claim 5, wherein the spring biases the rod towards the retracted position.

7. The plumbing device of claim 1, wherein the sleeve is movably positioned on the outer surface of the housing between a first end of the housing and a second end of the housing.

8. The plumbing device of claim 1, wherein the handles include threading engaging the sleeve.

9. The plumbing device of claim 1, wherein the rod defines a pin opening transversely through the rod, and wherein the pin is connected to the rod in the pin opening.

* * * * *